United States Patent [19]

Minamisaka et al.

[11] Patent Number: 5,597,941

[45] Date of Patent: Jan. 28, 1997

[54] PROCESS FOR PRODUCTION OF 5-AMINO-3-METHYLPYRAZOLE

[75] Inventors: Kazuya Minamisaka, Takaishi; Masahito Sekiguchi, Ibaraki; Kenji Saito, Hirakata, all of Japan

[73] Assignee: Sumitomo Chemical Company, Limited, Osaka, Japan

[21] Appl. No.: 366,017

[22] Filed: Dec. 29, 1994

Related U.S. Application Data

[63] Continuation of Ser. No. 141,988, Oct. 28, 1993, abandoned.

[30] Foreign Application Priority Data

Nov. 5, 1992 [JP] Japan .................................. 4-295689
Nov. 9, 1992 [JP] Japan .................................. 4-298702

[51] Int. Cl.$^6$ .................................................. C07C 253/14
[52] U.S. Cl. .................... 558/337; 558/355; 558/342; 558/462; 548/371.4
[58] Field of Search .................................. 558/337, 355, 558/342, 462; 548/371.4

[56] References Cited

U.S. PATENT DOCUMENTS

| | | | |
|---|---|---|---|
| 2,975,188 | 3/1961 | Gold et al. | 548/152 |
| 3,634,488 | 1/1972 | Morita et al. | 558/462 |
| 3,920,693 | 11/1975 | Ege | 548/371.4 |

FOREIGN PATENT DOCUMENTS

| | | |
|---|---|---|
| 0370357 | 5/1990 | European Pat. Off. . |
| 1224884 | 6/1960 | France . |
| 2044654 | 3/1972 | Germany . |
| 3714834 | 11/1988 | Germany . |
| 47-6179 | 4/1972 | Japan . |
| 50-96567 | 7/1975 | Japan . |
| 2134354 | 5/1990 | Japan . |
| 2279674 | 11/1990 | Japan . |

OTHER PUBLICATIONS

Vessiere, et al.; Compt. Rend., 253 (1961), pp. 676–677.
Vessiere, et al.; Compt. Rend., 255 (1962), pp. 3424–3426.
Bulletin De Societe Chimique De La France, vol. 1, No. 4, 1907, Paris, France, pp. 1071–1079, C. Moureu et al., "No. 165.—Condensation des hydrazines avec les nitriles acétyléniques et avec les nitriles beta–cétoniques", p. 1073, last paragraph—p. 1074, paragraph 1.
Tetrahedron Letters, No. 13, (1975) pp. 1101–1104, Z. T. Fomum et al.
Compt. Rend., vol. 143, (1906) pp. 1239–1242, Ch. Moureau et al.
Justus Liebigs Annalen Der Chemie, vol. 624, (1959) P. Kurz et al, pp. 1–25.
Bulletin De La Societe Chimique De France, No. 7–8, 1959, pp. 1268–1274, R. Vessiere.
Bulletin De La Societe Chimique De France, No. 7, 1968, pp. 2994–3000, F. Theron et al.
Chemical Abstracts, vol. 54, (1960) abstract No. 274f, Kurtz et al.
Chemical Abstracts, vol. 81, (1974) Abstract No. 105429x, Alcalde et al.
Chemical Abstracts, vol. 114, (1991) Abstract No. 185496e, Ogawa et al.
Chemical Abstracts, vol. 50, Abstract No. 4195g, Kurtz, (1956).
Chemical Abstracts, vol. 71, (1969) Abstract No. 80741w, Kimura et al.
Chemical Abstracts, vol. 111, (1989) Abstract No. 115168p, Lantzsch.
J. Heterocyclic Chem., vol. 19, (1982) pp. 1267–1273, Ege et al.
Chemical Abstracts, vol. 55, Abstract No. 11307h, Kurtz, (1961).
Chemical Abstracts, vol. 59, Abstract No. 441e, Vessiere et al., (1963).
Chemical Abstracts, vol. 55, Abstract No. 25988c, Gold et al., (1961).

Primary Examiner—Johann Richter
Assistant Examiner—John Peabody
Attorney, Agent, or Firm—Watson Cole Stevens Davis P.L.L.C.

[57] ABSTRACT

The process for producing 5-amino-3-methylpyrazole includes the steps of reacting 2,3-dichloropropene with a cyanogenating agent in the presence of a cuprous salt and water at a pH of 3–8 to obtain at least one intermediate selected from the group consisting of 3-chloro-3-butenonitrile and 2,3-butadienenitrile; reacting the at least one intermediate with a base in the presence of water at a pH of 12.5 or above to obtain 2-butynenitrile; and reacting the 2-butynenitrile with hydrazine. This process is advantageous in that it enables the production of 5-amino-3-methylpyrazole in high yield without using any reagent which may produce fire. 5-Amino-3-methylpyrazole is a useful intermediate for medicines, agricultural chemicals, photographic chemicals, etc.

15 Claims, No Drawings

PROCESS FOR PRODUCTION OF 5-AMINO-3-METHYLPYRAZOLE

This application is a continuation of application Ser. No. 08/141,998, filed Oct. 28, 1993 now abandoned.

BACKGROUND OF THE INVENTION

1. Field of the Invention

The present invention relates to a process for producing 2-butynenitrile, as well as to a process for industrially producing, from the 2-butynenitrile produced by said process, 5-amino-3-methylpyrazole which is a useful intermediate for production of medicines, agricultural chemicals and photographic chemicals.

2. Description of the Prior Art

For production of 2-butynenitrile, there has been known a process which comprises producing 3-bromo-3-butenonitrile from 2,3-dibromopropene and prussic acid and then reacting 3-bromo-3-butenonitrile with sodium carbonate [Compt. Rend., 253, 676 (1961) and 255, 3424 (1962)].

This process, however, produces 3-bromo-3-butenonitrile (a starting material for 2-butynenitrile) in low yield (26%) [Compt. Rend., 253, 676 (1961)] and has not been sufficient as a process for industrially producing 2-butynenitrile.

For production of 5-amino-3-methylpyrazole, there has been known a process which comprises producing 5-amino-3-methylpyrazole using 3-aminocrotononitrile as a starting material (JP-A-2-279674).

This process, however, has not been sufficient as a process for industrially producing 5-amino-3-methylpyrazole because the process uses a reagent having a risk of producing fire, that is, 3-aminocrotononitrile as a starting material is obtained by a method (disclosed in, for example, JP-A-2-134354) of reacting acetonitrile with a stoichiometric amount of an alkali metal or the hydride thereof (both of them generate hydrogen when contacted with water).

The present inventors found that 2-butynenitrile can be obtained in high yield, without using any reagent having the above-mentioned problem, by using a process comprising a step of cyanogenating 2,3-dichloropropene of good industrial availability to produce at least one intermediate selected from the group consisting of 3-chloro-3-butenonitrile and 2,3-butadienenitrile. The present inventors further found that the reaction of the thus obtained 2-butynenitrile with hydrazine gives 5-amino-3-methyl pyrazole in high yield. The finding has led to the completion of the present invention.

SUMMARY OF THE INVENTION

According to the present invention, there are provided:

a process for producing 2-butynenitrile which comprises the steps of:
(1) reacting 2,3-dichloropropene with a cyanogenating agent in the presence of a cuprous salt and water at a pH of 3–8 to obtain at least one intermediate selected from the group consisting of 3-chloro-3-butenonitrile and 2,3-butadienenitrile, and
(2) reacting the at least one intermediate with a base in the presence of water at a pH of 12.5 or above;

a process for producing 2-butynenitrile which comprises the steps of:
(1) reacting 2,3-dichloropropene with prussic acid in the presence of a cuprous salt, calcium carbonate and a polar solvent to obtain 3-chloro-3-butenonitrile, and
(2) reacting the 3-chloro-3-butenonitrile with a base in the presence of water at a pH of 12.5 or above;

a process for producing 2-butynenitrile which comprises the step of reacting 3-chloro-3-butenonitrile with a base in the presence of water at a pH of 12.5 or above to give rise to the dehydrochlorination and isomerization of 3-chloro-3-butenonitrile;

a process for producing 2-butynenitrile which comprises the step of reacting 2,3-butadienenitrile with a base in the presence of water at a pH of 12.5 or above to give rise to the isomerization of 2,3-butadienenitrile;

a process for producing 5-amino-3-methylpyrazole which comprises the step of reacting 2-butynenitrile with hydrazine;

a process for producing 5-amino-3-methylpyrazole which comprises the steps of:
(1) reacting 2,3-dichloropropene with a cyanogenating agent in the presence of a cuprous salt and water at a pH of 3–8 to obtain at least one intermediate selected from the group consisting of 3-chloro-3-butenonitrile and 2,3-butadienenitrile,
(2) reacting the at least one intermediate with a base in the presence of water at a pH of 12.5 or above to obtain 2-butynenitrile, and
(3) reacting the 2-butynenitrile with hydrazine; and a process for producing 5-amino-3-methylpyrazole, which comprises the steps of:
(1) reacting 2,3-dichloropropene with prussic acid in the presence of a cuprous salt, calcium carbonate and a polar solvent to obtain 3-chloro-3-butenonitrile,
(2) reacting the 3-chloro-3-butenonitrile with a base in the presence of water at a pH of 12.5 or above to obtain 2-butynenitrile, and
(3) reacting the 2-butynenitrile with hydrazine.

DETAILED DESCRIPTION OF THE INVENTION

First, description is made on the first aspect of the present invention, that is, a process for producing 2-butynenitrile, which comprises the steps of:
(1) reacting 2,3-dichloropropene with a cyanogenating agent in the presence of a cuprous salt and water at a pH of from 3 to 8, both inclusive, to obtain at least one intermediate selected from the group consisting of 3-chloro-3-butenonitrile and 2,3-butadienenitrile, and
(2) reacting the at least one intermediate with a base in the presence of water at a pH of 12.5 or above.

The cyanogenating agent used in step (1) includes prussic acid and prussic acid salts such as sodium prussate, potassium prussate and the like. The amount used of the cyanogenating agent is not particularly restricted but is usually within the range of from 1 to 2 moles per mole of 2,3-dichloropropene. The cuprous salt includes, for example, cuprous chloride and cuprous cyanide. The amount used of the cuprous salt is not particularly restricted but is usually within the range of from 0.01 to 1 mole, preferably within the range of from 0.05 to 0.3 mole, per mole of 2,3-dichloropropene. A copper powder may be used together with the cuprous salt in the reaction of step (1). Usually, the copper powder used has an approximate particle size of from 30 to 100 mesh, and may be used in an approximate amount of up to about 0.5 mole per mole of the cuprous salt.

The reaction of step (1) can be encouraged by allowing sodium iodide to be present in the reaction system. The amount used of sodium iodide is usually up to about 0.5 mole, preferably up to about 0.3 mole, per mole of 2,3-dichloropropene.

The reaction is usually conducted in the presence of water. The solvent that can be used together with water includes organic polar solvents (e.g. methanol, ethanol, ethylene glycol, dimethylformamide and dimethyl sulfoxide), hydrocarbon solvents (e.g. toluene, hexane and heptane), and mixed solvents thereof. The amount used of water and the solvent other than water is usually 1 to 10 times the weight of 2,3-dichloropropene.

The reaction is usually conducted at a pH of from 3 to 8, both inclusive, and produces 3-chloro-3-butenonitrile and/or 2,3-butadienenitrile. The proportion of the two compounds produced varies depending upon the pH of the reaction system. When the pH is low, 3-chloro-3-butenonitrile is produced in an increased amount and, when the pH is high, 2,3-butadienenitrile is produced in an increased amount. When the pH is kept within the range of from 3 inclusive to 6 exclusive, preferably within the range of from 3 inclusive to 5 inclusive, 3-chloro-3-butenonitrile is obtained as a main product. Meanwhile, when the pH is kept within the range of from 6 inclusive to 8 inclusive, 2,3-butadienenitrile is obtained as a main product.

Any of 3-chloro-3-butenonitrile and 2,3-butadienenitrile is converted to 2-butynenitrile by a reaction with a base in step (2); therefore, the species of the main product is not critical. In the reaction of 2,3-dichloropropene with the cyanogenating agent, when the pH of the reaction system is higher than 8, tar is formed violently and neither 3-chloro-3-butenonitrile nor 2,3-butadienenitrile are obtained. When the pH of the reaction system is lower than 3, substantially no reaction takes place.

When prussic acid is selected as a cyanogenating agent, it is preferable to conduct step (1) in the presence of an appropriate amount of a base or while adding a base stepwise, in order to keep the pH of the reaction system within the above-mentioned range. The base includes alkali metal hydroxides (e.g. sodium hydroxide and potassium hydroxide), alkaline earth metal hydroxides (e.g. calcium hydroxide and magnesium hydroxide), alkali metal carbonates (e.g. sodium carbonate and potassium carbonate), alkali metal bicarbonates (e.g. sodium hydrogen carbonate and potassium hydrogen carbonate), alkaline earth metal carbonates (e.g. calcium carbonate and magnesium carbonate), alkali metal salts of lower carboxylic acids (e.g. sodium formate and sodium acetate), alkali metal alcoholates (e.g. sodium methylate, sodium ethylate and potassium butoxide), and organic bases (e.g. triethylamine and pyridine). These bases can be used as they are or in the form of an aqueous solution or an aqueous suspension. Of these bases, preferable are calcium hydroxide and calcium carbonate. The amount used of the base used is not particularly restricted but is usually within the range of from 0.1 to 3 equivalents, preferably within the range of from 1 to 2 equivalents, per equivalent of 2,3-dichloropropene.

When a prussic acid salt is selected as a cyanogenating agent, an acid may be used as occasion demands depending upon the pH selected in addition to the above-mentioned base. Such an acid includes mineral acids (e.g. hydrochloric acid and sulfuric acid) and lower carboxylic acids.

The reaction of step (1) is conducted, for example, by adding 2,3-dichloropropene and a cyanogenating agent each independently or as a mixture by drops, to a mixture of a solvent and a cuprous salt. The reaction temperature is not particularly restricted but is usually within the range of from 50° to 120° C.

In the reaction of step (1), particularly when prussic acid is selected as a cyanogenating agent, 2,3-dichloropropene may be reacted with prussic acid in the presence of calcium carbonate, a cuprous salt and a polar solvent, in an autoclave at 90°–110° C. under tight sealing and pressure in order to avoid the vaporization of prussic acid, whereby 3-chloro-3-butenonitrile can be obtained in high yield. The polar solvent includes water, organic polar solvents (e.g. methanol, ethanol, ethylene glycol, demethylformamide, dimethyl sulfoxide and mixed solvents thereof).

After completion of the reaction, the products may be separated by operations such as filtration and layer separation, and if necessary extraction and the like. When an organic solvent is used in the reaction and/or the extraction, it can be removed by subjecting the reaction mixture or the extract each containing the above-mentioned nitriles to distillation in order to obtain the intended nitriles. If necessary, the nitriles may be purified by such a means as distillation or the like.

Then, description is made on step (2) of reacting the 3-chloro-3-butenonitrile or 2,3-butadienenitrile or the mixture thereof all obtained in step (1), with a base in the presence of water at a pH of 12.5 or above to obtain 2-butynenitrile. The reaction which may take place in this step include a reaction in which 3-chloro-3-butenonitrile is dehydrochlorinated and isomerized to 2-butynenitrile, a reaction in which 2,3-butadienenitrile is isomerized to 2-butynenitrile, and a reaction in which a mixture of 3-chloro-3-butenonitrile and 2,3-butadienenitrile is dehydrochlorinated and isomerized to 2-butynenitrile.

Any of the above reactions proceeds in the presence of water. Water may be added to the reaction system in the form of an aqueous reaction mixture containing 3-chloro-3-butenonitrile and/or 2,3-butadienenitrile obtained in step (1) or an aqueous base solution, or may be put into a reaction container beforehand. The amount used of water is sufficient if it enables the pH measurement of the reaction system; however, it usually falls within the approximate range of from 1 to 10 times the weight of the raw material nitrile or nitriles.

In the reaction, there may be used the same organic solvent as used in the reaction of 2,3-dichloropropene with prussic acid. There may be further used, if necessary, a phase transfer catalyst, etc.

Next, description is made on the reaction in which 3-chloro-3-butenonitrile is reacted with a base in the presence of water at a pH of 12.5 or above to obtain 2-butynenitrile. The base includes alkali metal alcoholates (e.g. sodium methylate, sodium ethylate and potassium butoxide), and alkali metal hydroxides (e.g. sodium hydroxide and potassium hydroxide). Sodium hydroxide and potassium hydroxide are particularly preferable. These bases are used in the form of an aqueous solution or an aqueous suspension.

In the reaction, a base is added to 3-chloro-3-butenonitrile in the presence of water, or 3-chloro-3-butenonitrile and a base are simultaneously added into a reactor in the presence of water, whereby the pH of the reaction system is made 12.5 or above and 2-butynenitrile is obtained. When the pH of the reaction system is adjusted to 6 inclusive to 12.5 exclusive, the dehydrochlorination of 3-chloro-3-butenonitrile proceeds and 2,3-butadienenitrile as an intermediate is obtained; however, this 2,3-butadienenitrile can be finally converted to 2-butynenitrile by raising the pH of the reaction system to 12.5 or above.

The reaction temperature is not particularly restricted but is usually within the range of from 0° to 100° C., preferably within the range of from 0° to 50° C.

After completion of the reaction, operations such as filtration and layer separation, and if necessary extraction and the like are carried out, whereby 2-butynenitrile can be obtained. When an organic solvent is used in the reaction and/or the extraction, it can be removed by subjecting the reaction mixture or the extract each containing the above-mentioned nitriles to distillation in order to isolate the intended product. The product may be subjected as occasion demands to operations such as distillation and the like to obtain 2-butynenitrile.

Next, description is made on the reaction in which 2,3-butadienenitrile is isomerized to 2-butynenitrile.

2,3-Butadienenitrile, which is a starting material in this isomerization reaction, can be prepared by reacting 3-chloro-3-butenonitrile with a base in the presence of water at a pH of 6 to below 12.5 to promote the dehydrochlorination, or alternatively, by reacting 2,3-dichloropropene with a cyanogenating agent. 2,3-Butadienenitrile may be supplied to the isomerization reaction without being isolated from the reaction mixture, or alternatively, it may be supplied to the isomerization reaction after being isolated from the reaction mixture.

The base usable in the reaction includes, for example, alkali metal hydroxides (e.g. sodium hydroxide and potassium hydroxide) and alkali metal alcoholates (e.g. sodium methylate, sodium ethylate and potassium butoxide). These bases can be used as they are or in the form of an aqueous solution or an aqueous suspension. Of these bases, sodium hydroxide and potassium hydroxide are particularly preferable.

The isomerization reaction can be conducted by adding a base to 2,3-butadienenitrile in the presence of water. It can be conducted by simultaneously adding 2,3-butadienenitrile and a base into a reactor in the presence of water. It also can be conducted by adding 2,3-butadienenitrile by drops to a base in the presence of water. In any of these cases, the pH of the reaction system is kept at 12.5 or above. Thus, 2-butynenitrile can be obtained. The reaction temperature is not particularly restricted but is usually within the range of from 0° to 100° C., preferably within the range of from 0° to 50° C.

In the reaction in which a mixture of 3-chloro-3-butenonitrile and 2,3-butadienenitrile is subjected to dehydrochlorination and isomerization to obtain 2-butynenitrile, a base may be added to the above two materials. Alternatively, the above two materials may be added to a base. Alternatively, the above two materials and a base may be added simultaneously. In any of these cases, the pH of the reaction system is kept at 12.5 or above to promote dehydrochlorination and isomerization simultaneously or stepwise, whereby 2-butynenitrile can be obtained.

The base used in the reaction may be appropriately selected from those bases used in the reactions in which either 3-chloro-3-butenonitrile or 2,3-butadienenitrile is converted to 2-butynenitrile. It is used in an amount enabling the necessary pH control of the reaction system. Of these bases, sodium hydroxide and potassium hydroxide are preferable and sodium hydroxide is particularly preferable.

The reaction temperature is not particularly restricted but is usually within the range of from 0° to 100° C., preferably within the range of from 0° to 50° C.

The thus formed 2-butynenitrile can be separated usually by subjecting the reaction mixture to filtration and layer separation and, when an organic solvent is used, by conducting distillation to remove the solvent. The separated 2-butynenitrile can be purified by a means such as distillation, column chromatography or the like.

Next, description is made on the process for producing 5-amino-3-methylpyrazole by reacting 2-butynenitrile with hydrazine.

The term hydrazine refers to anhydrous hydrazine or to hydrazine formed by the reaction of a base with a salt between hydrazine and an acid, such as hydrazine hydrochloride, hydrazine acetate or the like. However, hydrazine hydrate is usually used. The amount used of hydrazine is not particularly restricted but is usually within the range of from 1 to 2 moles per mole of 2-butynenitrile.

The reaction of 2-butynenitrile with hydrazine is conducted in the presence or absence of a solvent. The solvent may be water, an alcohol (e.g. methanol, ethanol, butanol) or an ether (e.g. diethyl ether, diisopropyl ether). The amount used of the solvent is not particularly restricted.

The reaction is preferably conducted by adding 2-butynenitrile or its solution in the above solvent by drops to hydrazine hydrate or its aqueous solution. The reaction can also be conducted by simultaneously pouring into a reactor 2-butynenitrile or its solution and hydrazine or its aqueous solution. The reaction can also be conducted by adding hydrazine hydrate or its aqueous solution by drops to 2-butynenitrile or its aqueous solution. The reaction temperature is usually within the range of from 20° to 120° C.

The 2-butynenitrile used in the above reaction may be any of the reaction mixtures obtained in the above-mentioned reactions for obtaining 2-butynenitrile, or may be 2-butynenitrile itself isolated from said reaction mixtures by ordinary post-treatments.

The reaction mixture containing 5-amino-3-methylpyrazole, obtained in the above process is subjected to an ordinary post-treatment, whereby 5-amino-3-methylpyrazole can be obtained.

The present invention is hereinafter described in more detail by way of Examples. However, the present invention is not restricted to these Examples.

EXAMPLE 1

186.3 Grams (1.80 moles) of cuprous chloride, 15.7 g (0.25 mole) of a copper powder and 2,400 g of water were placed in a 10-liter separable flask. The flask contents were stirred and kept at 65° C. 97.2 Grams (3.60 moles) of prussic acid and 655.4 g (1.77 moles in terms of calcium hydroxide) of a 20% aqueous calcium hydroxide slurry were simultaneously poured into the flask. The pH of the resulting mixture was 6.5. The mixture was then heated to 80° C. To the mixture kept at 80° C. was added by drops a mixture of 1,344 g (12.00 moles) of 2,3-dichloropropene and 388.4 g (14.40 moles) of prussic acid in 2.5 hours. During the period, 2,571.3 g (6.94 moles in terms of calcium hydroxide) of a 20% calcium hydroxide slurry was added by drops to keep the pH of the system at 6.0–7.0. The resulting mixture was kept at the same temperature for an additional 2 hours. During the period, 398.9 g (1.08 moles in terms of calcium hydroxide) of a 20% calcium hydroxide slurry was added by drops to keep the pH of the system at 6.0–7.0.

After completion of the reaction, the reaction mixture was cooled to 20° C. The cooled mixture was subjected to filtration and layer separation to obtain 531.9 g of brown oily crude 2,3-butadienenitrile containing 371.1 g (5.70 moles) of 2,3-butadienenitrile and 60.9 g (0.60 moles) of 3-chloro-3-butenonitrile.

To 531.9 g of this brown oily crude 2,3-butadienenitrile was added 81.4 g (0.57 mole in terms of sodium hydroxide) of a 28% aqueous sodium hydroxide solution in order to keep the reaction system at a pH of 12.5 or above. The mixture was allowed to react at 30° C. for 1 hour. After completion of the reaction, the reaction mixture was allowed to stand and subjected to layer separation to obtain 379.3 g of a reddish brown oil. The aqueous layer was extracted with 80.0 g of dichloromethane. The resultant dichloromethane layer was combined with the oil. Distilling the thus combined mixture gave 322.4 g of a fraction containing 305.3 g (4.69 moles, yield: 39.0% based on 2,3-dichloropropene) of 2-butynenitrile and 5.86 g (0.090 moles, yield: 0.75% based on 2,3-dichloropropene) of 2,3-butadienenitrile.

EXAMPLE 2

Into a 100-ml flask was fed 7.17 g of an oil containing 6.51 g (0.10 mole) of 2,3-butadienenitrile and 0.63 g (0.0097 mole) of 2-butenenitrile. Thereto was dropwise added 1.45 g (0.010 mole in terms of sodium hydroxide) of a 28% aqueous sodium hydroxide solution so as to keep the pH of the resultant mixture at 12.5 or above, and the mixture was allowed to react at 30° C. for 1 hour. After completion of the reaction, the reaction mixture was allowed to stand for layer separation to obtain 5.48 g of a reddish brown oil. The aqueous layer was extracted with 40.0 g of dichloromethane. The resulting dichloromethane layer was combined with the reddish brown oil. Distilling the thus combined mixture gave 6.21 g of a fraction containing 5.91 g (0.091 mole) of 2-butynenitrile and 0.17 g (0.0026 mole) of 2,3-butadienenitrile. The yield of 2-butynenitrile was 83.0%.

EXAMPLE 3

186.3 Grams (1.80 moles) of cuprous chloride, 15.7 g (0.25 mole) of a copper powder and 2,400 g of water were placed in a 10-liter separable flask. The flask contents were stirred and kept at 65° C. 97.2 Grams (3.60 moles) of prussic acid and 580.7 g (1.57 moles in terms of calcium hydroxide) of a 20% aqueous calcium hydroxide slurry were simultaneously poured into the flask. The pH of the resulting mixture was 3.5. The mixture was then heated to 80° C. To the mixture kept at 80° C. was added by drops a mixture of 1,344 g (12.00 moles) of 2,3-dichloropropene and 388.4 g (14.40 moles) of prussic acid in 4.5 hours. During the period, 1,948.7 g (5.26 moles in terms of calcium hydroxide) of a 20% calcium hydroxide slurry was added by drops to keep the pH of the system at 3.3–3.9. The resulting mixture was kept at the same temperature for an additional 2 hours. During the period, 353.0 g (0.95 mole in terms of calcium hydroxide) of a 20% calcium hydroxide slurry was added by drops to keep the pH of the system at 3.3–3.9.

After completion of the reaction, the reaction mixture was cooled to 20° C. The cooled mixture was subjected to filtration and layer separation to obtain 1,142.0 g of brown oily crude 3-chloro-3-butenonitrile containing 985.6 g (9.71 moles, yield: 80.9% based on 2,3-dichloropropene) of 3-chloro-3-butenonitrile and 19.2 g (0.30 mole, yield: 2.5% based on 2,3-dichloropropene) of 2,3-butadienenitrile. 80.0 Grams (0.36 mole in terms of sodium hydroxide) of a 18% aqueous sodium hydroxide solution was placed in a 200-ml flask. Thereto was added by drops the brown oily crude 3-chloro-3-butenonitrile (35.3 g, 0.30 mole in terms of 3-chloro-3-butenonitrile) at 10° C. in 30 minutes. After completion of the addition, the resultant mixture was heated to 20° C. and kept at that temperature for 1 hour. During the period from the addition to the end of the temperature keeping, the pH of the reaction system was kept at 12.5 or above. Then, the heated mixture was allowed to stand for layer separation to obtain 21.19 g of a reddish brown oil. The aqueous layer was extracted with 60.0 g of dichloromethane. The resulting dichloromethane layer was combined with the reddish brown oil. Distilling the thus combined mixture gave 20.76 g of a fraction containing 16.41 g (0.252 mole) of 2-butynenitrile and 2.00 g (0.031 mole) of 2,3-butadienenitrile. The yield of 2-butynenitrile was 68.0% based on 2,3-dichloropropene and the yield of 2,3-butadienenitrile was 8.4% based on 2,3-dichloropropene.

EXAMPLE 4

Into a 200-ml flask was placed 80.0 g (0.36 mole in terms of sodium hydroxide) of a 18% aqueous sodium hydroxide solution. Thereto was added by drops, at 10° C. in 30 minutes, 35.57 g of an oil containing 30.45 g (0.30 mole) of 3-chloro-3-butenonitrile and 3.24 g (0.050 mole) of 2,3-butadienenitrile. After completion of the addition, the resultant mixture was heated to 20° C. and kept at the same temperature for 1 hour. During the period from the addition to the end of the temperature keeping, the pH of the reaction system was kept at 12.5 or above. The heated mixture was allowed to stand for layer separation to obtain 21.46 g of a reddish brown oil. The aqueous layer was extracted with 60.0 g of dichloromethane. The resulting dichloromethane layer was combined with the reddish brown oil. Distilling the thus combined mixture gave 21.98 g of a fraction containing 20.54 g (0.316 mole) of 2-butynenitrile and 1.00 g (0.015 mole) of 2,3-butadienenitrile. The yield of 2-butynenitrile was 90.3% and the yield of 2,3-butadienenitrile was 4.3%.

EXAMPLE 5

Into a 300-ml flask were placed 120 g of water and 31.3 g of an oil containing 28.02 g (0.276 mole) of 3-chloro-3-butenonitrile and 1.56 g (0.0239 mole) of 2,3-butadienenitrile. Thereto was added by drops 43.4 g (0.304 mole as sodium hydroxide) of a 28% aqueous sodium hydroxide solution at 20° C. After completion of the addition, the resultant mixture was kept at 20° C. for 5 hours while keeping the pH of the system at 12.5 or above and monitoring the decrease of 2,3-butadienenitrile by gas chromatography. The resulting mixture was allowed to stand for layer separation to obtain 16.91 g of a reddish brown oil. The aqueous layer was extracted with 120.0 g of dichloromethane. The resulting dichloromethane layer was combined with the reddish brown oil. Distilling the thus combined mixture gave 20.15 g of a fraction containing 15.28 g (0.235 mole) of 2-butynenitrile and 0.84 g (0.013 mole) of 2,3-buadienenitrile. The yield of 2-butynenitrile was 78.3% and the yield of 2,3-butadienenitrile was 4.3%.

EXAMPLE 6

45.57 g (0.326 mole in terms of sodium cyanide) of a 35% aqueous sodium cyanide solution and 12.10 g (0.119 mole in terms of hydrochloric acid) of 36% hydrochloric acid were simultaneously poured, at 65° C. with stirring, into a 1-liter flask containing 15.63 g (0.15 mole) of cuprous chloride and 249 g of water, to allow the resulting mixture to have a pH of 3.2. The resultant mixture was heated to 80° C. Into the heated mixture were simultaneously poured, at 80° C. in 5 hours, 111.0 g (0.98 mole) of 2,3-dichloropropene and 139.92 g (1.00 mole in terms of sodium cyanide) of a 35% aqueous sodium cyanide solution. During the period, the pH of the system was kept at 3.4–3.8 by adding 11.70 g (0.116 mole in terms of hydrochloric acid) of 36% hydrochloric acid by drops. The mixture was kept at 80° C. for for an additional 5 hours. During the period, the pH of the system was kept at 3.6–3.8 by adding 28.23 g (0.198 mole in terms of sodium hydroxide) of a 28% aqueous sodium hydroxide solution by drops.

After completion of the reaction, the reaction mixture was cooled to 28° C. and subjected to filtration and layer separation to obtain 86.5 g of a brown oil containing 75.88 g (0.748 mole, yield: 77.4% based on 2,3-dichloropropene) of 3-chloro-3-butenonitrile and 3.04 g (0.047 mole, yield: 4.8% based on 2,3-dichloropropene) of 2,3-butadienenitrile.

34.71 Grams of the brown oil was added by drops, at 10° C. in 30 minutes, to 80.0 g (0.36 mole in terms of sodium hydroxide) of a 18% aqueous sodium hydroxide solution placed in a 200-ml flask. After completion of the addition, the resultant mixture was heated to 20° C. and kept at the same temperature for 1 hour. During the period, the pH of the reaction system was kept at 12.5 or above. The reaction mixture was allowed to stand for layer separation to obtain 20.36 g of a reddish brown oil. The aqueous layer was extracted with 60.0 g of dichloromethane. The resulting dichloromethane layer was combined with the reddish brown oil. Distilling the thus combined mixture gave 17.11 g of a purified 2-butynenitrile fraction containing 15.97 g (0.245 mole, yield: 63.2% based on 2,3-dichloropropene) of 2-butynenitrile and 0.80 g (0.012 mole, yield: 3.1% based on 2,3-dichloropropene) of 2,3-butadienenitrile.

EXAMPLE 7

13.23 Grams of a 2-butynenitrile fraction containing 0.193 mole of 2-butynenitrile and 0.007 mole of 2,3-butadienenitrile were added by drops, at 80° C. in 7 hours, to 26.05 g (0.208 mole in terms of hydrazine hydrate) of 40% hydrazine hydrate placed in a 100-ml flask. The resultant mixture was kept at 80° C. for 2 hours, then cooled to room temperature and extracted with ethyl acetate. Removing the solvent from the resulting ethyl acetate layer by distillation gave 20.7 g of crude 5-amino-3-methylpyrazole (purity: 85%, 0.182 mole, yield: 91.4% based on the total of 2-butynenitrile and 2,3-butadienenitrile).

Purifying the crude 5-amino-3-methylpyrazole by silica gel column chromatography gave 17.46 g of purified 5-amino-3-methylpyrazole (purity: 99%, 0.178 mole, yield: 89% based on the total of 2-butynenitrile and 2,3-butadienenitrile).

EXAMPLE 8

20.73 Grams of a 2-butynenitrile fraction containing 0.288 mole of 2-butynenitrile and 0.006 mole of 2,3-butadienenitrile was added by drops, at 70°–80° C. in 40 minutes, to 18.79 g (0.300 mole in terms of hydrazine hydrate) of 80% hydrazine hydrate placed in a 100-ml flask. The resultant mixture was kept at 70°–80° C. for 4 hours and then cooled to room temperature. The cooled mixture was extracted with ethyl acetate. Removing the solvent from the resulting ethyl acetate layer by distillation gave 28.11 g of crude 5-amino-3-methylpyrazole (purity: 86%, 0.249 mole, yield: 84.7% based on the total of 2-butynenitrile and 2,3-butadienenitrile).

Purifying the crude 5-amino-3-methylpyrazole by silica gel column chromatography gave 23.64 g of 5-amino-3-methylpyrazole (purity: 99%, 0.241 mole, yield :82.1% based on the total of 2-butynenitrile and 2,3-butadienenitrile).

EXAMPLE 9

186.3 Grams (1.80 moles) of cuprous chloride, 15.7 g (0.25 mole) of a copper powder and 2,400 g of water were placed in a 10-liter separable flask. The flask contents were stirred and kept at 65° C. 97.2 Grams (3.60 moles) of prussic acid and 580.7 g (1.57 moles in terms of calcium hydroxide) of a 20% aqueous calcium hydroxide slurry were simultaneously poured into the flask. The pH of the resulting mixture was 3.5. The mixture was then heated to 80° C. To the mixture kept at 80° C. was added by drops a mixture of 1,344 g (12.00 moles) of 2,3-dichloropropene and 388.4 g (14.4 moles) of prussic acid in 4.5 hours. During the period, 1,948.7 g (5.26 moles in terms of calcium hydroxide) of a 20% calcium hydroxide slurry was added by drops to keep the pH of the system at 3.3–3.9. The resulting mixture was kept at the same temperature for an additional 2 hours. During the period, 353.0 g (0.95 mole in terms of calcium hydroxide) of a 20% calcium hydroxide slurry was added by drops to keep the pH of the system at 3.3–3.9.

After completion of the reaction, the reaction mixture was cooled to 20° C. The cooled mixture was subjected to filtration and layer separation to obtain 1,142 g of brown oil containing 985.6 g (9.71 moles, yield: 80.9% based on 2,3-dichloropropene) of 3-chloro-3-butenonitrile and 19.2 g (0.30 mole, yield : 2.5% based on 2,3-dichloropropene) of 2,3-butadienenitrile.

80.0 Grams (0.36 mole in terms of sodium hydroxide) of a 18% aqueous sodium hydroxide solution was placed in a 200-ml flask. Thereto was added by drops 35.3 g of the brown oil at 10° C. in 30 minutes while keeping the pH of the system at 12.5 or above. After completion of the addition, the resultant mixture was heated to 20° C. and kept at that temperature for 1 hour. Then, the heated mixture was allowed to stand for layer separation to obtain 21.19 g of a reddish brown oil. The aqueous layer was extracted with 60.0 g of dichloromethane. The resulting dichloromethane layer was combined with the reddish brown oil. Distilling the thus combined mixture gave 17.46 g of a fraction containing 16.41 g (0.252 mole) of 2-butynenitrile and 0.70 g (0.01 mole) of 2,3-butadienenitrile. The yield of 2-butynenitrile was 68.0% based on 2,3-dichloropropene and the yield of 2,3-butadienenitrile was 2.7% based on 2,3-dichloropropene.

25.04 Grams (0.200 mole in terms of hydrazine) of 40% hydrazine hydrate was placed in a 100-ml flask. It was kept at 90° C. Thereto was added 13.29 g of the 2-butynenitrile fraction by drops in 8 hours. The resultant mixture was kept at the same temperature for 1 hour, and then returned to room temperature. The thus treated mixture was extracted with ethyl acetate. Removing the solvent from the resulting ethyl acetate layer by distillation gave 37.27 g of an oil containing 17.38 g of 5-amino-3-methylpyrazole (yield: 89.5%).

EXAMPLE 10

45.57 Grams (0.326 mole in terms of sodium cyanide) of a 35% aqueous sodium cyanide solution and 12.10 g (0.119 mole in terms of hydrochloric acid) of 36% hydrochloric acid were simultaneously poured, at 65° C. with stirring, into a 1-liter flask containing 15.63 g (0.15 mole) of cuprous chloride and 249 g of water, to allow the resulting mixture to have a pH of 3.2. The resultant mixture was heated to 80° C. Into the heated mixture were simultaneously poured, at 80° C. in 5 hours, 111.0 g (0.98 mole) of 2,3-dichloropropene and 139.92 g (1.00 mole in terms of sodium cyanide) of a 35% aqueous sodium cyanide solution. During the period, the pH of the system was kept at 3.4–3.8 by adding 11.70 g (0.116 mole in terms of hydrochloric acid) of 36% hydrochloric acid by drops. The resulting mixture was kept at 80° C. for an additional 5 hours. During the period, the pH of the system was kept at 3.6–3.8 by adding 28.23 g (0.198 mole in terms of as sodium hydroxide) of a 28% aqueous sodium hydroxide solution by drops.

After completion of the reaction, the reaction mixture was cooled to 28° C. and subjected to filtration and layer separation to obtain 86.5 g of a brown oil containing 75.88 g (0.748 mole, yield: 77.4% based on 2,3-dichloropropene) of 3-chloro-3-butenonitrile, 3.04 g (0.047 mole, yield: 4.8% based on 2,3-dichloropropene) of 2,3-butadienenitrile and 0.43 g (0.007 mole, yield: 0.7% based on 2,3-dichloropropene) of 2-butynenitrile.

34.71 Grams of the brown oil was added by drops to 80.0 g (0.36 mole in terms of sodium hydroxide) of a 18% aqueous sodium hydroxide solution placed in a 200-ml flask, at 10° C. in 30 minutes with the pH of the system being kept at 12.5 or above. After completion of the addition, the resultant mixture was heated to 20° C. and kept at the same temperature for 1 hour. The heated mixture was allowed to stand for layer separation to obtain 20.36 g of a reddish brown oil. The aqueous layer was extracted with 60.0 g of dichloromethane. The resulting dichloromethane layer was combined with the reddish brown oil. Distilling the thus combined mixture gave 17.11 g of a purified 2-butynenitrile fraction containing 15.97 g (0.245 mole, yield: 63.2% based on 2,3-dichloropropene) of 2-butynenitrile and 0.80 g (0.012 mole, yield: 3.1% based on 2,3-dichloropropene) of 2,3-butadienenitrile.

13.28 g of the above 2-butynenitrile was added by drops, at 80° C. in 7 hours, to 25.05 g (0.200 mole in terms of hydrazine hydrate) of 40% hydrazine hydrate placed in a 100-ml flask. The resultant mixture was kept at the same temperature for 2 hours and then cooled to room temperature. The cooled mixture was extracted with ethyl acetate. Removing the solvent from the resulting acetate layer by distillation gave 37.88 g of an oil containing 17.48 g (0.180 mole) of crude 5-amino-3-methylpyrazole (yield: 90%).

EXAMPLE 11

Into a 50-ml autoclave were placed 0.015 g (0.15 mmole) of cuprous chloride, 0.006 g (0.09 mmole) of a copper powder, 0.165 g (1.65 mmoles) of calcium carbonate and 0.4 ml of methanol. The autoclave contents were cooled to 4° C. Thereto were added 0.089 g (3.3 mmoles) of prussic acid and 0.333 g (3.0 mmoles) of 2,3-dichloropropene. The resultant mixture was heated to 100° C. and kept at the same temperature for 10 hours with stirring. After completion of the reaction, the reaction mixture was filtered to remove solids. Distilling the filtrate gave 0.227 g (2.19 mmole) of 3-chloro-3-butenonitrile (purity: 98%, yield: 72.9%).

0.227 Gram of the above-obtained 3-chloro-3-butenonitrile was added by drops, at 10° C. in 5 minutes, to 0.584 g (2.628 mmoles in terms of sodium hydroxide) of a 18% aqueous sodium hydroxide solution placed in a 10-ml flask. After completion of the addition, the resultant mixture was heated to 20° C. and kept at the same temperature for 1 hour. During the period from the addition to the end of the temperature keeping, the pH of the reaction system was kept at 12.5 or above. The heated mixture was allowed to stand for layer separation to obtain 0.151 g of a reddish brown oil. The aqueous layer was extracted with 2 g of dichloromethane. The resulting dichloromethane layer was combined with the reddish brown oil. Distilling the thus combined mixture gave 0.137 g of a fraction containing 0.120 g (1.84 mmoles) of 2-butynenitrile and 0.014 g (0.220 mmoles) of 2,3-butadienenitrile. The yield of 2-butynenitrile was 61.3% based on 2,3-dichloropropene and the yield of 2,3-butadienenitrile was 7.3% based on 2,3-dichloropropene.

EXAMPLE 12

The 2-butynenitrile obtained in Example 11 was reacted with hydrazine in the same manner as in Example 10, whereby 5-methyl-3-aminopyrazole was obtained.

According to the present invention, 2-butynenitrile can be obtained in high yield without using any alkali metal hydride having a risk of producing fire. Moreover, 5-amino-3-methylpyrazole can be produced easily by reacting the thus obtained 2-butynenitrile with hydrazine.

What is claimed is:

1. A process for producing 2-butynenitrile which comprises the steps of:
   (1) reacting 2,3-dichloropropene with prussic acid in the presence of a cuprous salt, calcium carbonate and a polar solvent to obtain 3-chloro-3-butenonitrile, and
   (2) reacting the 3-chloro-3-butenonitrile with a base in the presence of water at a pH of 12.5 or above to produce 2-butynenitrile.

2. A process for producing 2-butynenitrile which comprises the step of reacting 3-chloro-3-butenonitrile with a base in the presence of water at a pH of 12.5 or above to give rise to the dehydrochlorination and isomerization of 3-chloro-3-butenonitrile to produce 2-butynertrile.

3. A process for producing 2-butynenitrile which comprises the step of reacting 2,3-butadienenitrile with a base in the presence of water at a pH of 12.5 or above to give rise to the isomerization of 2,3-butadienenitrile to produce 2-butynertrile.

4. A process for producing 5-amino-3-methyl-pyrazole which comprises the steps of:
   (1) reacting 2,3-dichloropropene with a cyanogenating agent in the presence of a cuprous salt and water at a pH of 3–8 to obtain at least one intermediate selected from the group consisting of 3-chloro-3-butenonitrile and 2,3-butadienenitrile,
   (2) reacting the at least one intermediate with a base in the presence of water at a pH of 12.5 or above to obtain 2-butynenitrile, and
   (3) reacting the 2-butynenitrile with a hydrazine compound selected from the group consisting of anhydrous hydrazine and a hydrazine formed by the reaction of a base with a salt between hydrazine and an acid to produce 5-amino-3-methyl-pyrazole.

5. A process for producing 5-amino-3-methyl-pyrazole which comprises the steps of:
   (1) reacting 2,3-dichloropropene with prussic acid in the presence of a cuprous salt, calcium carbonate and a polar solvent to obtain 3-chloro-3-butenonitrile,
   (2) reacting the 3-chloro-3-butenonitrile with a base in the presence of water at a pH of 12.5 or above to obtain 2-butynenitrile, and
   (3) reacting the 2-butynenitrile with a hydrazine compound selected from the group consisting of anhydrous hydrazine and a hydrazine formed by the reaction of a base with a salt between hydrazine and an acid to produce 5-amino-3-methyl-pyrazole.

6. A process for producing 2-butynenitrile which comprises the steps of:
   (1) reacting 2,3-dichloropropene with a cyanogenating agent in the presence of a cuprous salt and water at a pH of 3–8 to obtain at least one intermediate selected from the group consisting of 3-chloro-3-butenonitrile and 2,3-butadienenitrile, and (2) reacting the at least one intermediate with a base in the presence of water at a pH of 12.5 or above to produce 2-butynenitrile, wherein the amount of cyanogenating agent used in step (1) falls within the range of from 1 to 2 moles per mole of 2,3-dichloropropene, the amount of cuprous salt used in step (1) falls with the range of from 0.01 to 1 mole per mole of 2,3-dichloropropene, the reaction temperature of step (1) falls within the range of from 50° to 120° C., and the reaction temperature of step (2) falls within the range of from 0° to 100° C.

7. A process for producing 2-butynenitrile which comprises the steps of:

(1) reacting 2,3-dichloropropene with prussic acid in the presence of a cuprous salt, calcium carbonate and a polar solvent to obtain 3-chloro-3-butenonitrile, and (2) reacting the 3-chloro-3-butenonitrile with a base in the presence of water at a pH of 12.5 or above to produce 2-butynenitrile wherein the amount of prussic acid used in step (1) falls within the range of from 1 to moles per mole of 2,3-dichloropropene, the amount of cuprous salt used in step (1) falls within the range of from 0.01 to 1 mole per mole of 2,3-dichloropropene, the amount of calcium carbonate used in step (1) falls within the range of from 0.01 to 3 equivalents per equivalent of 2,3-dichloropropene, the reaction temperature of step (1) falls with the range of from 50° to 120° C., and the reaction temperature of step (2) falls within the range of from 0° to 100° C.

8. The process according to claim 3, wherein the reaction temperature falls within the range of from 0° to 100° C.

9. The process according to claim 3, wherein the reaction temperature falls within the range of from 0° to 100° C.

10. The process according to claim 4, wherein the amount of cyanogenating agent used in step (1) falls within the range of from 1 to 2 moles per mole of 2,3-dichloropropene, the amount of cuprous salt used in step (1) falls within the range of from 0.01 to 1 mole per mole of 2,3-dichloropropene, the reaction temperature of step (1) falls within the range of from 50° to 120° C., the reaction temperature of step (2) falls within the range of from 0° to 100° C., the amount of hydrazine used in step (3) falls within the range of from 1 to 2 moles per mole of 2-butynenitrile, and the reaction temperature of step (3) falls within the range of from 20° to 120° C.

11. The process according to claim 5, wherein the amount of prussic acid used in step (1) falls within the range of from 1 to 2 moles per mole of 2,3-dichloropropene, the amount of cuprous salt used in step (1) falls within the range of from 0.01 to 1 mole per mole of 2,3-dichloropropene, the reaction temperature of step (1) falls within the range of from 50° to 120° C., the reaction temperature of step (2) falls within the range of from 0° to 100° C., the amount of hydrazine used in step (3) falls within the range of from 1 to 2 moles per mole of 2-butynenitrile, and the reaction temperature of step (3) falls within the range of from 20° to 120° C.

12. A process for producing 2-butynenitrile which comprises the steps of:

(1) reacting 2,3-dichloropropene with a cyanogenating agent in the presence of a cuprous salt and water at a pH of 3–8 to obtain at least one intermediate selected from the group consisting of 3-chloro-3-butenonitrile and 2,3-butadienenitrile, and (2) reacting the at least one intermediate with a base in the presence of water at a pH of 12.5 or above to produce 2-butynenitrile, wherein the amount of cyanogenating agent used in step (1) falls within the range of from 1 to 2 moles per mole of 2,3-dichloropropene, the amount of cuprous salt used in step (1) falls within the range of from 0.01 to 1 mole per mole of 2.3-dichloropropene, the reaction temperature of step (1) falls within the range of from 50° to 120° C., and the reaction temperature of step (2) falls within the range of from 0° to 10° C., wherein the cyanogenating agent is at least one member selected from the group consisting of prussic acid and prussic acid salts.

13. The process according to claim 10, wherein the cyanogenating agent is at least one member selected from the group consisting of prussic acid and prussic acid salts.

14. The process according to claim 4, wherein the hydrazine formed by the reaction of a base with a salt between hydrazine and an acid is selected from the group consisting of hydrazine hydrochloride and hydrazine acetate.

15. The process according to claim 5, wherein the hydrazine formed by the reaction of a base with a salt between hydrazine and an acid is selected from the group consisting of hydrazine hydrochloride and hydrazine acetate.

* * * * *